United States Patent [19]
Grace et al.

[11] Patent Number: 5,527,259
[45] Date of Patent: Jun. 18, 1996

[54] MAGNETIC FIELD INDUCTION MULTI-PULSE THERAPY

[75] Inventors: Robert J. Grace; Avenel G. Grace, both of Adelaide, Australia

[73] Assignee: Circuitry Systems Limited, Gibraltar

[21] Appl. No.: 270,497

[22] Filed: Jul. 5, 1994

[51] Int. Cl.$^6$ .................................................. A61N 1/00
[52] U.S. Cl. .................................................. 600/14
[58] Field of Search .......................... 600/9, 10, 13–15

[56] References Cited

U.S. PATENT DOCUMENTS

| | | | |
|---|---|---|---|
| 2,438,605 | 3/1948 | Hart | 600/14 |
| 3,915,151 | 10/1975 | Kraus | 600/9 |
| 4,911,686 | 3/1990 | Thaler | 600/14 |
| 4,974,114 | 11/1990 | Kammerer | 600/9 X |
| 4,993,413 | 2/1991 | McLeod et al. . | |
| 5,014,699 | 5/1991 | Pollack et al. | 600/14 X |
| 5,030,196 | 7/1991 | Inoue | 600/14 |
| 5,085,626 | 2/1992 | Frey . | |

FOREIGN PATENT DOCUMENTS

| | | |
|---|---|---|
| 0048451 | 9/1981 | European Pat. Off. . |
| 0459402A2 | 5/1991 | European Pat. Off. . |
| 1466337 | 3/1974 | United Kingdom . |
| 2143131 | 2/1985 | United Kingdom . |
| 2156679 | 10/1985 | United Kingdom . |
| 89/05673 | 6/1989 | WIPO . |
| 90/06341 | 5/1991 | WIPO . |

OTHER PUBLICATIONS

Copy of a paper presented at "The 4th Ocenaia Symposium Da Complimentary Medicine–Gold Coast", Oct. 10, 1992 The Health Implication of Magnetic Fields.

*Primary Examiner*—Lee S. Cohen
*Assistant Examiner*—Samuel Gilbert
*Attorney, Agent, or Firm*—Merchant, Gould, Smith, Edell, Welter & Schmidt

[57] ABSTRACT

A method and apparatus for therapeutic treatment wherein pulsed, alternating current, electrical signals are applied to an applicator coil adjacent an area to be treated to produce multi-rhythmic, pulsed, alternating magnetic fields which have a therapeutic effect on the treated area. The frequency of the magnetic fields is in the range 0.5 Hz to 25 Hz and the waveform includes higher harmonics to approximate natural waveforms measured in the body, such as by an EEG.

16 Claims, 3 Drawing Sheets

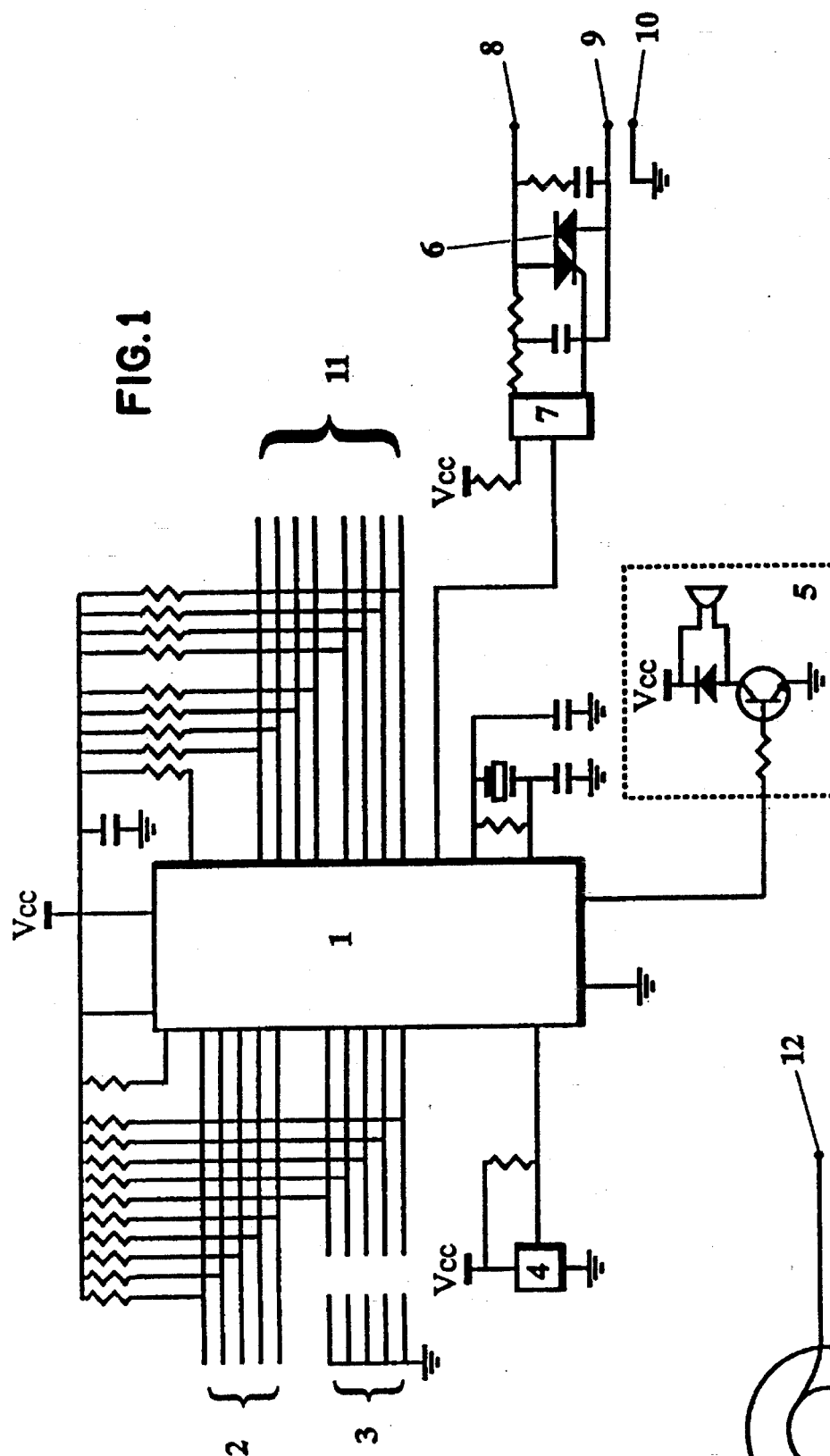
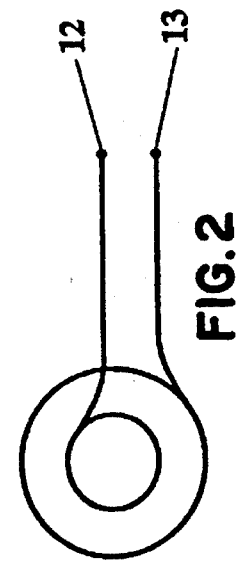

MAGNETIC FIELD INDUCTION MULTI-PULSE THERAPY

This invention relates to an improved Magnetic Field Induction Therapy device and an improved method of treatment using Magnetic Field Induction Therapy. The method and the device utilise pulsed alternating magnetic fields of specific characteristics which have been found to be therapeutic.

BACKGROUND ART

The therapeutic value of magnetic fields has been known for more than two thousand years. Permanent magnets placed on or adjacent an animal or human body have been used for pain relief and blood circulation improvement. It is also known to use pulsating magnetic fields for medical and therapeutic purposes.

For over 50 years the use of electro-magnetic fields has been known to be more beneficial than static or permanent magnetic fields. The most common devices use a generator unit to produce a pulsing or time-varying electric current which is fed into a wire-wound coil or coils to produce an electromagnetic field.

In most commercially available prior art devices direct current (D.C.) pulses are used to energise the applicator coils. These prior art devices have proven effective in providing temporary pain relief and promoting repair of damaged tissue. The inventors have found that an enhanced effect can be obtain by applying multi-rhythm bio-waveforms of pulsed alternating magnetic fields.

Medical science and clinical testing (using an electroencephalogram) have established that the predominant brain wave activity is a spiked alternating waveform at a frequency of between 8 Hz and 13 Hz. This is known as the 'alpha' rhythm. Other rhythms detected by an EEG are the 'beta' rhythm at frequencies above 13 Hz, the 'theta' rhythm at frequencies between 4 Hz and 7 Hz and the 'delta' rhythm at frequencies below 4 Hz. Other less common rhythms ('mu'—9 Hz, 'lambda'—4–6 Hz) have also been measured.

It has also been established that the terrestrial magnetic field has a predominant pulsing of 9.6 Hz with Schumann Resonance frequencies of 7.83 Hz to 7.96 Hz. The terrestrial magnetic field and other naturally occurring fields have an induced electrical effect on all living matter at the cellular level. This effect is due to the paramagnetic nature of materials in living matter such as DNA and blood. Blood contains iron which is paramagnetic and therefore affected by magnetic fields and the DNA in every cell has positive and negative regions. The basis of magnetic therapy is that artificially produced fields can have a beneficial effect on living tissue by interaction with the paramagnetic components.

Electrical potential has been measured across cell walls. This potential is maintained by the movement of ions and in particular, $Na^+$, $K^+$, $Cl^-$, and $HCO^-$. Normal cell potentials vary from $-60$ mV in some muscles to as much as $-120$ mV in myocardial cells. This movement of ions is known to have a profound influence on the inflammatory process of living tissue. Cell wall potential differences tend to attract positive ions into and negative ions out of the cell, resulting in a reduction in cell potential, an increase in fluid(oedema) and a triggering, under certain conditions, of pain mechanisms. A pulsed alternating magnetic field can influence the net ion flux through the cell membrane to restore the normal cell potential and $Na^+$ and $K^+$ balance, and release encephalin, endorphin and other chemicals to inhibit or modify pain signal transmission.

OBJECT OF THE INVENTION

It is an object of the present invention to provide a method and apparatus which provide therapeutic effects by the use of extremely low frequency, pulsed alternating magnetic fields applied to living tissue.

DISCLOSURE OF THE INVENTION

In one form of the invention there is provided an apparatus for therapeutic treatment comprising:

a generator unit adapted to provide alternating current;

a control means in electrical connection with said generator unit and adapted to receive as input alternating current from the generator unit and to provide electrical signals as output;

said electrical signals being multi-rhythmic pulsed alternating signals at a frequency in the range 0.5 Hz to 25 Hz; and one or more applicator coils in electrical connection with said control means and adapted to convert the electrical signals to magnetic fields.

In a further form of he invention there is proposed a method of therapeutic treatment including the steps of:

locating one or more applicator coils adjacent an area to be treated;

applying electrical signals having frequency, amplitude and pulse characteristics to said applicator coils so as to produce multi-rhythmic, pulsed, alternating magnetic fields in the vicinity of the coils; and adjusting the frequency, amplitude and pulse characteristics so as to produce a pulsating magnetic field having therapeutic effect in the said area to be treated.

BRIEF DESCRIPTION OF DRAWINGS

To further assist in understanding the invention reference will be made to the following drawings in which:

FIG. 1 Shows a schematic of one preferred embodiment of a control means for the invention;

FIG. 2 Shows a sketch of a preferred form of applicator coil;

DETAILED DESCRIPTION OF DRAWINGS

Figure 3:
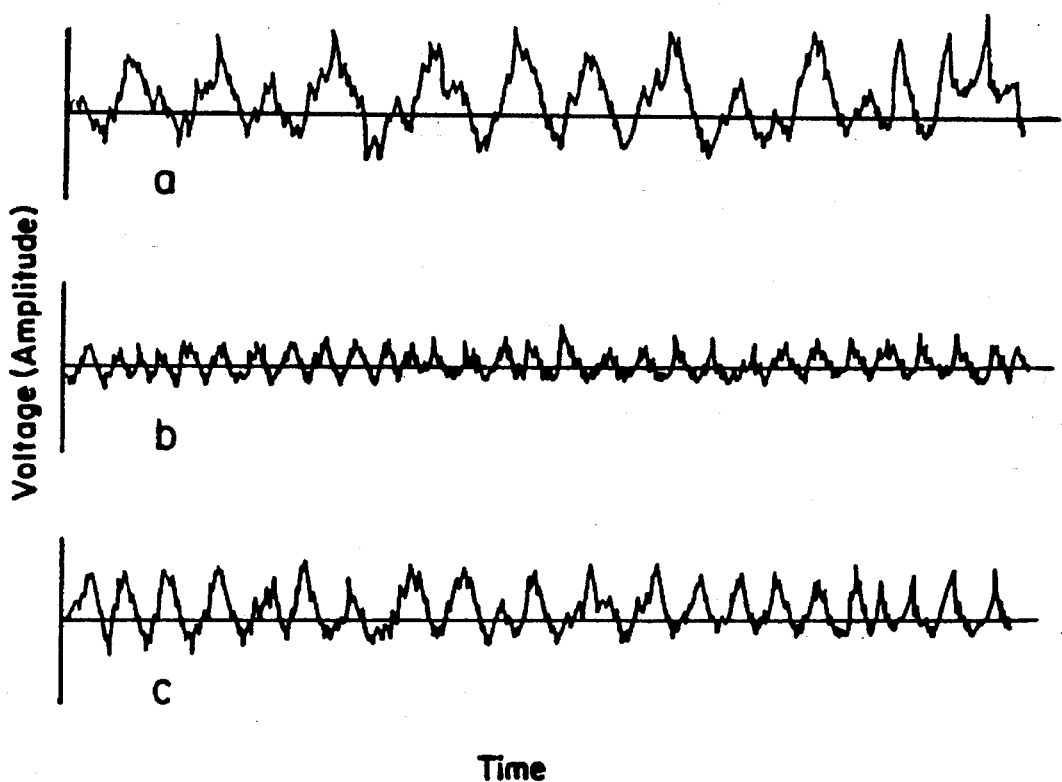
FIG. 3 Show typical EEG waveforms of a human brain.

Referring now to the drawings in detail there is shown in FIG. 1 a block diagram of the control means of one preferred embodiment of a magnetic field induction multi-pulse therapy device. The control means includes a microprocessor 1 which controls the characteristics of signals applied to the applicator coils. In the embodiment shown the microprocessor is a 68HC705C8F microprocessor which operates from a 5 volt supply (Vcc), other similar devices may also be used. A number of control lines 2 allow the user to select between a range of values for some of the magnetic field parameters. For example the control lines allow the setting of the duration of treatment and the primary frequency of the applied magnetic field. One control line is a start/stop switch.

In the preferred embodiment the duration of treatment may be selected as 10, 15, 20, 25 or 30 minutes and the frequencies may be chosen as 0.5, 1, 2, 3, 4, 5, 8, 10, 12, 15 or 18 Hz. The frequencies are chosen for their beneficial effect and it will be noted that certain frequencies known to be have negative effects (such as 13 Hz which is known to cause disorientation and to induce epileptic fits) have been omitted. A further setting gives an automatic programme of 30 sec at 2 Hz, 60 sec at 4 Hz, 90 sec at 8 Hz and 120 sec at 12 Hz repeated four times for a total treatment time of 20 minutes. Another automatic setting is incorporated which continuously repeats intervals of a chosen treatment until manually stopped. For example, if a treatment of 20 minutes at 0.5 Hz is chosen this treatment will be applied followed by a 20 minute pause followed by the same treatment and so on until stopped.

At power up the device automatically resets to a default setting of 0.5 Hz for 20 minutes otherwise when a treatment is completed the device resets ready to repeat the last treatment.

The inventors have found that this specific sequence of ascending pulse frequencies provides even greater benefits than available from single frequency treatments, particularly in a reduction in the time needed to obtain relief and/or healing.

The use of a microprocessor based control means allows for configuration of the device for a number of different applications. The mode lines 3 can be enabled using wire patches to configure the Magnetic Field Induction Therapy device for human, equine or canine use. The mode lines can also be used to disable some features such as the reset controller 4 or the timer buzzer 5. The reset controller 4 resets the microprocessor to the default settings after a treatment has been completed. The timer buzzer 5 gives an audible indication that a period of treatment has ended.

The control means also includes a triac 6 which is coupled to the microprocessor 1 by opto-coupler 7. An AC signal of 18 volts peak-to-peak at line frequency (ie. 50 Hz or 60 Hz) is provided at input 8. The signals from the microprocessor 1 control the operation of the triac 6 to provide the desired pulsed AC signal at output 9. The input AC signal is unfiltered and therefore contains higher harmonics. The arrangement of capacitors and resistors associated with the triac are chosen to allow some higher harmonics to appear at the output 9. As described below this results in an output electrical signal more closely approximating the natural electrical activity of a body. The connections 9 and 10 connect to the applicator coil connections 12 and 13 shown in FIG. 2.

The 18 volt AC signal is provided from a generator unit which is a step-down transformer wound to provide secondary alternating current voltage sources of 18 volts and 7 volts from a primary alternating current voltage source such as a 240 volt or 120 volt household supply. The 7 volt signal is rectified and powers a 5 volt regulator which provides the Vcc source. Although 18 volts AC is used in this embodiment it will be appreciated that other voltages will also be appropriate depending on the specific electrical characteristics of the applicator coils. In an alternate embodiment the voltage is selectable through the control lines 2.

The device is provided with a five volt liquid crystal display which is driven by display lines 11. The LCD indicates the treatment time remaining and the frequency of treatment. Other indications, such as the operation mode or program details can be shown if desired.

A typical applicator coil is shown in FIG. 2. The coil is a pad type having an outside diameter of 170 mm and approximately 800 turns of copper wire with an impedance of preferably 15 Ohms. A circular or oval design is chosen to avoid undesirable eddy currents in the magnetic field. Such coils may be covered with a suitable thermal insulating material, cushion layers of a foam plastic and enclosed in a vinyl or other suitable covering envelope.

Other versions may be in the shape of cylindrical tube applicators with layers of coil winding around the circumference. Further versions may have a number of coils connected electrically in series, parallel or a combination of configurations and enclosed in a mat, pad or mattress. The inventors have found that such multiple coil arrangements should have each coil wound in the same direction, be arranged symmetrically, be of similar dimensions and equal electrical resistance, and be individually insulated to minimise interference fields and eddy currents which are of a non-beneficial nature.

Specifically shaped coils have been found to produce concentrated projection of the magnetic field which has benefits in specific applications such as dental analgesic. In each case the electrical characteristics of the coil must suit pulsed alternating current provided from the control means.

In a second preferred embodiment a version of the device which can operate from a direct current low voltage power source is provided. This device is designed for use in an automobile, truck or bus and can be plugged into the cigarette lighter of a car. Instead of a step-down transformer to covert a household power supply to 18 volts a step-up transformer is used to step-up the DC voltage and a known DC to AC inverter circuit is used to produce the AC source. The Vcc supply is derived directly from the DC source. The inverted voltage is pulsed at a frequency of either 50 Hz or 60 Hz. Harmonic characteristics are added to be similar to that obtained from the AC version described in detail above.

The second embodiment can be particularly useful for relieving muscle cramp and fatigue in long distance drivers. Packets or bursts of pulses at a rhythmic rate with frequencies between 10 Hz and 20 Hz have been found useful for this purpose without causing sleepiness or lack of concentration.

FIG. 3 shows examples of three forms of measured brain waves with amplitude on the vertical axes and time on the horizontal axes. FIG. 3a shows 'delta' waves at below 4 HZ typical of some stages of sleep; FIG. 3b shows 'beta' waves at a frequency above 13 Hz typical of an awake and alert state; FIG. 3c shows 'alpha' waves at between 8 Hz and 13 Hz typical of an awake but relaxed state. It is clear from these traces that the primary electrical activity of the brain (and the rest of the body) is not a clean sinusoidal waveform but a more complex convolution of a number of waveforms.

Figure 4:
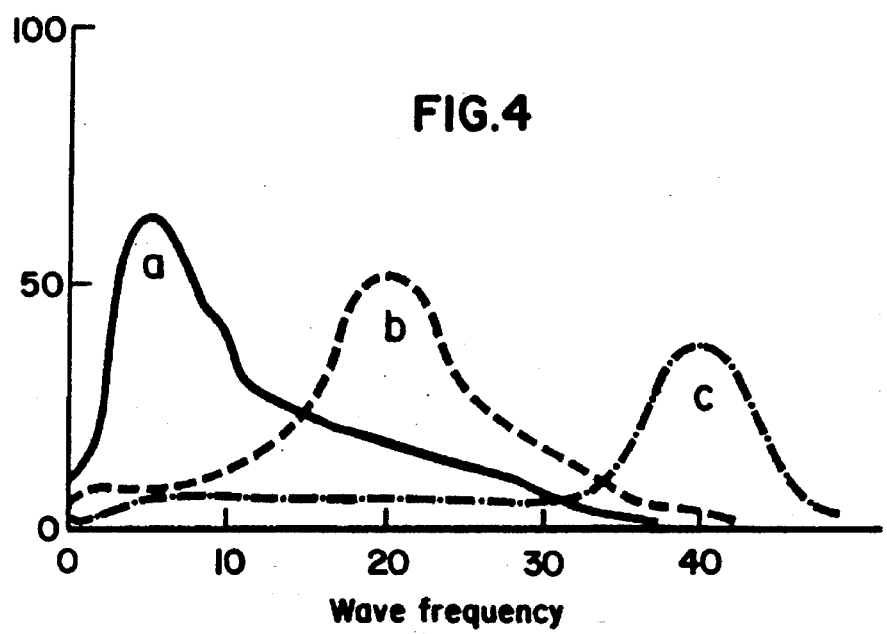
FIG. 4 Shows a frequency analysis of brain waves during different levels of activity.

An analysis of the active frequencies during different levels of activity is shown in FIG. 4. When asleep lower frequencies predominate as shown in trace a. When awake but relaxed there is a spread of slightly higher frequencies as shown in trace b and the spread of frequencies is higher again when alert as in trace c. The inventors have recognised that most regeneration of the bodies systems occur during sleep and have therefore found that lower frequencies are most beneficial for promoting repair and recovery with the Magnetic Field Induction Therapy device.

Figure 5:
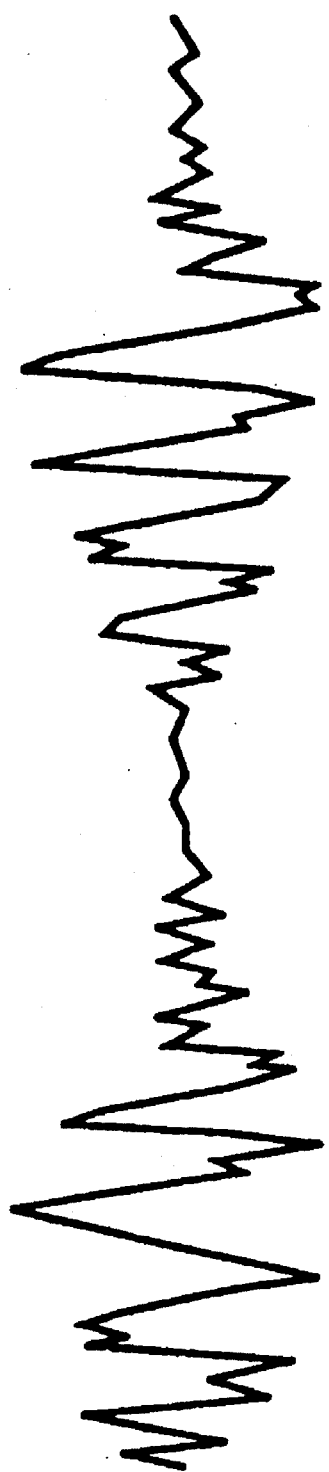
FIG. 5 Shows a typical waveform of the present invention.

A typical waveform produced by the apparatus of the present invention is shown in FIG. 5. As mentioned above the waveform includes higher harmonic frequencies and therefore approximates somewhat the waveforms shown in FIG. 3.

Because the waveform is AC there is no time averaged current induced in the treated tissue and therefore the bodies systems are not unbalanced. However, because there are transient currents induced the bodies natural curative mechanisms are enhanced.

The inventors have found through experimentation that the method and apparatus herein disclosed are useful for temporary relief of pain, arthritis, rheumatism and back ache, for alleviating circulatory and respiratory problems, for reducing inflammation and for treating tendonitis and sports injuries. In particular, they have found that at frequencies between 0.5 Hz and 9 Hz there is a mild constrictive effect in blood flow which can be important for the treatment of acute stages of injury to reduce swelling, infection and inflammation. At frequencies between 12 Hz and 18 Hz the major blood vessels and capillaries are dilated, allowing increased blood flow which is necessary for the secondary stages of healing.

The purpose of this specification has been to describe the invention without limiting the invention to any specific embodiment. Those skilled in the relevant art will be able to conceive of variations to the specific embodiments which will nonetheless fall within the scope of the spirit of the invention.

The claims defining the invention are as follows:

1. An apparatus for therapeutic treatment comprising:
   a generator unit for providing alternating current;
   a control means, in electrical connection with said generator unit, for receiving as input alternating current from the generator unit and for providing electrical signals as output;
   said electrical signals being multi-rhythmic pulsed alternating signals at a frequency in a range of 0.5 Hz to 25 Hz; and one or more applicator coils, in electrical connection with said control means, for converting the electrical signals to magnetic fields.

2. The apparatus of claim 1 wherein the generator unit includes a step-down transformer for converting a primary alternating current voltage source to a secondary alternating current voltage source wherein the secondary alternating current voltage source has a voltage in a range of 15 volts to 50 volts.

3. The apparatus of claim 1 wherein the generator unit includes a step-down transformer for converting a primary alternating current voltage source to a secondary alternating current voltage source wherein the secondary alternating current voltage source has a voltage of 18 volts.

4. The apparatus of claim 1 wherein the generator unit includes a step-up transformer and DC to AC inverter circuit for, in combination, converting a direct current voltage source to an alternating current voltage source with a voltage in a range of 15 volts to 50 volts and a frequency of either 50 Hz or 60 Hz.

5. The apparatus of claim 1 wherein the generator unit includes a step-up transformer and DC to AC inverter circuit for, in combination, converting a direct current voltage source to an alternating current voltage source with a voltage of 18 volts and a frequency of 50 Hz.

6. The apparatus of claim 1 wherein the control means comprises a microprocessor and a triac, wherein the microprocessor provides signals to control the operation of the triac and the control means further comprises an arrangement of resistors and capacitors in electrical connection with the triac for converting alternating current to multi-rhythmic pulsed alternating electrical signals.

7. The apparatus of claim 1 further comprising display means for displaying operating parameters of the apparatus.

8. The apparatus of claim 1 wherein the applicator coils are of wire-wound construction.

9. The apparatus of claim 1 wherein the electrical signals approximate natural waveforms found in the human body.

10. A method of therapeutic treatment including the steps of:
    locating one or more applicator coils adjacent an area to be treated;
    applying electrical signals having frequency, amplitude and pulse characteristics to said applicator coils so as to produce multi-rhythmic, pulsed, alternating magnetic fields in a vicinity of the coils; and
    adjusting the frequency, amplitude and pulse characteristics so as to produce a pulsating magnetic field having therapeutic effect in the area to be treated.

11. The method of claim 10 wherein the step of applying electrical signals includes applying signals with a frequency of 0.5 Hz for a time period between zero minutes and thirty minutes.

12. The method of claim 10 wherein the step of applying electrical signals includes applying a sequence of signals, said sequence comprising applying signals having a 2 Hz frequency for 30 seconds followed by signals having a 4 Hz frequency for 60 seconds followed by having a 8 Hz frequency for 90 seconds followed by having a 12 Hz frequency for 120 seconds and repeating said sequence four times for a total treatment time of 20 minutes.

13. The method of claim 10 wherein the step of adjusting the frequency, amplitude and pulse characteristics includes programming a microprocessor to automatically adjust the frequency, amplitude and pulse characteristics.

14. The method of claim 10 wherein the step of applying electrical signals includes repetitively applying at intervals a chosen treatment until manually stopped.

15. The apparatus of claim 10 wherein the electrical signals approximate natural waveforms found in the human body.

16. A method of therapeutic treatment including the steps of:
    locating one or more applicator coils adjacent an area to be treated;
    applying electrical signals having frequency, amplitude and pulse characteristics to said applicator coils so as to produce multi-rhythmic, pulsed, alternating magnetic fields in a vicinity of the coils, wherein the step of applying electrical signals includes applying a sequence of signals, said sequence comprising applying signals having a 2 Hz frequency for 30 seconds followed by signals having a 4 Hz frequency for 60 seconds followed by having a 8 Hz frequency for 90 seconds followed by having a 12 Hz frequency for 120 seconds and repeating said sequence a plurality of times; and
    adjusting the frequency, amplitude and pulse characteristics so as to produce a pulsating magnetic field having therapeutic effect in the area to be treated.

* * * * *